United States Patent
Li et al.

(10) Patent No.: US 11,642,316 B2
(45) Date of Patent: *May 9, 2023

(54) WATER-SOLUBLE CURCUMIN MIXTURE WITH HIGH BIOAVAILABILITY AND PREPARATION METHOD AND APPLICATION THEREOF

(71) Applicants: Honglong Li, Luohe (CN); Ziheng Jin, Luohe (CN); Linzheng Li, Luohe (CN); Xiaosong Xu, Luohe (CN); Di Wang, Luohe (CN); Chunfeng Yu, Luohe (CN); Wenjin Zhang, Luohe (CN); Huiting Xia, Luohe (CN)

(72) Inventors: Honglong Li, Luohe (CN); Ziheng Jin, Luohe (CN); Linzheng Li, Luohe (CN); Xiaosong Xu, Luohe (CN); Di Wang, Luohe (CN); Chunfeng Yu, Luohe (CN); Wenjin Zhang, Luohe (CN); Huiting Xia, Luohe (CN)

(73) Assignee: HENAN ZHONGDA HENGYUAN BIOTECHNOLOGY STOCK CO., LTD., Henan (CN)

( * ) Notice: Subject to any disclaimer, the term of this patent is extended or adjusted under 35 U.S.C. 154(b) by 19 days.

This patent is subject to a terminal disclaimer.

(21) Appl. No.: 17/473,974

(22) Filed: Sep. 13, 2021

(65) Prior Publication Data
US 2022/0347107 A1    Nov. 3, 2022

(30) Foreign Application Priority Data
Apr. 30, 2021   (CN) .......................... 202110484550.5

(51) Int. Cl.
*A61K 9/48*   (2006.01)
*A23L 33/15*   (2016.01)
*A61K 31/12*   (2006.01)
*A61K 31/375*   (2006.01)

(52) U.S. Cl.
CPC ............ *A61K 9/4833* (2013.01); *A23L 33/15* (2016.08); *A61K 31/12* (2013.01); *A61K 31/375* (2013.01)

(58) Field of Classification Search
CPC .... A61K 9/4833; A61K 31/12; A61K 31/375; A23L 33/15
See application file for complete search history.

(56) References Cited

FOREIGN PATENT DOCUMENTS

| CN | 1283237 C | 11/2006 |
|---|---|---|
| CN | 102283373 A | 12/2011 |
| CN | 103272245 A | 9/2013 |
| CN | 104922105 A | 9/2015 |
| CN | 107213467 A | 9/2017 |
| CN | 107712543 A | 2/2018 |
| CN | 109846865 A | 6/2019 |

*Primary Examiner* — Robert A Wax
*Assistant Examiner* — Olga V. Tcherkasskaya

(57) ABSTRACT

A method for preparing a water-soluble curcumin mixture with high bioavailability includes the following steps: A) dissolving curcumin, vitamin C and ascorbyl palmitate in an ethanol aqueous solution, evaporating ethanol under reduced pressure, and vacuum drying to obtain a curcumin-vitamin C-ascorbyl palmitate co-crystal; B) high-speed emulsifying the curcumin-vitamin C-ascorbyl palmitate co-crystal and a wall material colloidal solution under vacuum, sequentially conducting a two-stage wet grinding, a homogenization and a potential adjustment to obtain an emulsified body; and C) subjecting the emulsified body to microencapsulation with a wall material twice and drying to obtain the water-soluble curcumin.

9 Claims, 2 Drawing Sheets

WATER-SOLUBLE CURCUMIN MIXTURE WITH HIGH BIOAVAILABILITY AND PREPARATION METHOD AND APPLICATION THEREOF

This application claims priority to Chinese Patent Application No. 202110484550.5, filed on Apr. 30, 2021, which is incorporated by reference for all purposes as if fully set forth herein.

TECHNICAL FIELD

The invention related to food technology, and a high bioavailability water-soluble curcumin mixture and a preparation method and application thereof.

BACKGROUND TECHNIQUE

Curcumin is a natural polyphenol obtained by extracting, refining, crystallizing and drying the dried roots of the perennial herb of the ginger family Curcuma longa (Curcuma longa L.). Curcumin contains three main components: curcumin ($C_{21}H_{20}O_6$, molecular weight 368), monodemethoxy curcumin ($C_{21}H_{18}O_5$, molecular weight 338), and double-demethoxy curcumin ($C_{21}H_{16}O_4$, molecular weight 308). Curcumin has good heat resistance, reduction resistance and strong coloring ability. As a raw material for food colorants and seasonings, it has a long history of consumption. Curcumin is easily soluble in ethanol, glacial alkyd, and propylene glycol, but is basically insoluble in water, which limits its application effect and application range.

As the raw material of curcumin, curcumin is a traditional Chinese medicinal material, first reported in "Tang Materia Medica." Modern medical research shows that curcumin has good anti-inflammatory, antioxidant, free radical scavenging, tumor suppression, cardiovascular protection and other pharmacological effects, and has good preventive and therapeutic effects on various inflammations and pathological changes. However, the practical applications are limited by curcumin's poor water solubility and low bioavailability.

Scientific research shows that the increase in water solubility of natural products will be beneficial to the body's absorption. Therefore, there is a need to improve the solubility of curcumin in water and prepare curcumin with excellent water solubility. There are published methods on improving the solubility, for example, CN 109846865A, CN 103272245A, CN107712543A. These methods use n-hexane, ethanol, ethyl acetate solvents to dissolve curcumin, phospholipids, or cyclodextrin, etc. The use of large amount of these organic solvents poses a higher safety risk, and there will be more solvent residues in subsequent products. CN102283373A and CN 104922105A disclose the use synthetic emulsifiers, such as Tween and polyglycerol esters. Because synthetic emulsifiers have strict limits in the scope and amount of use in GB2760 (the National Standards of China 2760), they have a greater impact on the flavor of the product. In CN107213467A, the solubility of curcumin preparations in water is only increased by 1.5 times. In CN1283237C, the relative bioavailability is 205.47%, and the effect is not obvious.

SUMMARY OF THE INVENTION

In view of these, the technical problem to be solved by the present invention is to provide a high bioavailability water-soluble curcumin mixture and its preparation method and application. The preparation method provided by the present invention does not require synthetic emulsifiers and is solvent-free in the preparation process. The obtained curcumin mixture has excellent water solubility, and has been verified by animal experiments, and the relative bioavailability is 10 to 18 times or more.

In one embodiment, the present invention provides a method for preparing a water-soluble curcumin mixture with high bioavailability. The method includes the following steps: A) dissolving curcumin, vitamin C and ascorbyl palmitate in an ethanol aqueous solution, evaporating ethanol under reduced pressure, and vacuum drying to obtain a curcumin-vitamin C-ascorbyl palmitate co-crystal; B) high-speed emulsifying the curcumin-vitamin C-ascorbyl palmitate co-crystal and a wall material colloidal solution under vacuum, sequentially conducting a two-stage wet grinding, a homogenization and a potential adjustment to obtain an emulsified body; and C) subjecting the emulsified body to microencapsulation with a wall material twice and drying to obtain the water-soluble curcumin mixture.

In another embodiment, a mass ratio of curcumin, vitamin C and ascorbyl palmitate is 100:(0.001-30):(0.001-30).

In another embodiment, in step A), curcumin, vitamin C, ascorbyl palmitate and ethanol aqueous solution are heated at 0-60° C.; ethanol is evaporated under a pressure of 0.05 MPa to 1.0 MPa and at 25° C. to 100° C.

In another embodiment, the wall material colloid solution includes one or more selected from the group consisting of sodium starch octenyl succinate, hydroxypropyl starch, acetate starch, carboxymethyl starch, phosphate starch, arabic gum, ghatti gum, xanthan gum, pullulan, fucoidan, trehalose, and lactose; the wall material colloidal solution further includes a filler, and the filler is maltodextrin, microcrystalline cellulose, lactitol, erythritol, maltitol, sorbitol, α-cyclodextrin, β-cyclodextrin, γ-cyclodextrin, or a combination therefore; and the wall material colloid solution has a wall material colloid concentration of 5 wt % to 65 wt % and a filler concentration of 5 wt % to 65 wt %.

In another embodiment, the two-stage wet grinding includes a first grinding and a second grinding; the first grinding uses zirconia beads with diameter of 0.3 mm-0.4 mm and is conducted at a speed of 500 rpm to 3500 rpm for 1 to 10 hours; and the second grinding uses zirconia beads with diameter of 0.1 mm-0.2 mm and is conducted at a speed of 500 rpm to 3500 rpm for 1 to 10 hours.

In another embodiment, the high-speed emulsifying is conducted under a pressure of 0.05 MPa-0.1 Mpa, preferably, 0.075 MPa-0.095 MPa and at 10° C.-90° C., preferably 25° C.-60° C.; the homogenization is conducted under 100 MPa-200 MPa, preferably 130 MPa-180 Mpa; and the potential adjustment uses a Zeta potential modifier selected from the group consisting of sodium hexametaphosphate, sodium polyphosphate, sodium pyrophosphate, and sodium tripolyphosphate, and a colloidal emulsion potential is adjusted to −10 mv to −60 mv, preferably −30 mv to −50 mv.

In another embodiment, the wall material is starch, maltodextrin, or a mixture thereof, and a DE value of maltodextrin is 5-20; and the microencapsulation is conducted at a drying inlet air temperature of 160° C. to 200° C., an outlet air temperature of 70° C. to 100° C., and a bottom air temperature of 70° C. to 90° C.

In another embodiment, the water-soluble curcumin mixture has a curcumin-vitamin C-ascorbyl palmitate co-crystal concentration of 0.01 wt % to 70 wt %, preferably 5 wt % to 40 wt %.

In another embodiment, the present application discloses a water-soluble curcumin mixture prepared by the method of the present invention.

In another embodiment, the present application discloses an application of the water-soluble curcumin mixture in food, health food or medicine.

The results show that the water-soluble curcumin mixture of the present invention has significantly improved solubility and excellent water solubility, and has been verified by animal absorption experiments (rats), and its bioavailability has been increased by 10 to 18 times compared with the raw material curcumin.

DETAILED DESCRIPTION

Figure 1:
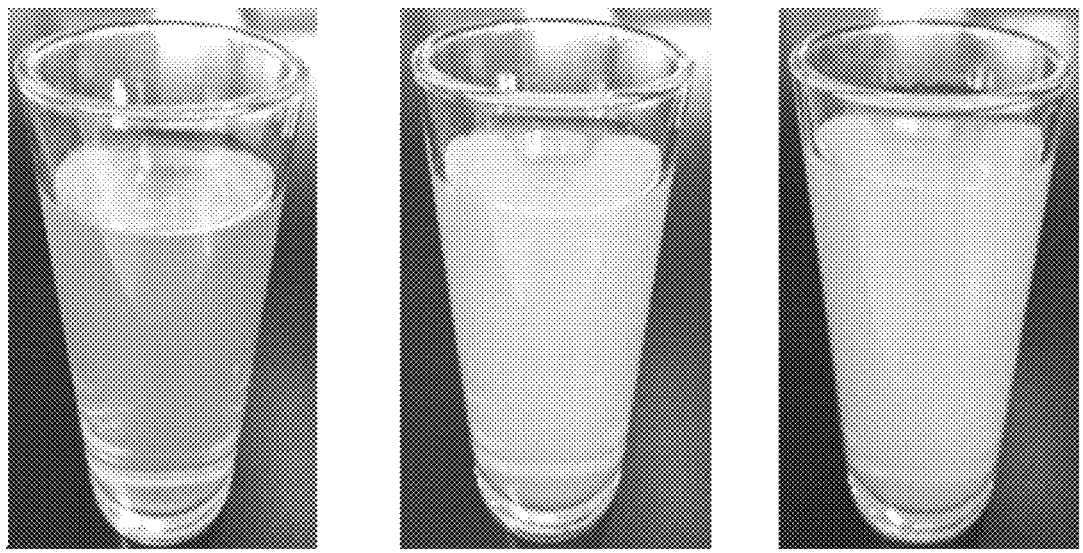
FIG. 1 is a photo showing the solubility of the curcumin mixture of Example 1 in water.

The present invention provides a method for preparing water-soluble curcumin mixture with high bioavailability, which includes the following steps:

A) dissolving curcumin, vitamin C (VC) and ascorbyl palmitate in an ethanol aqueous solution, evaporating ethanol under reduced pressure, and vacuum drying to obtain a curcumin-vitamin C-ascorbyl palmitate co-crystal;

B) high-speed emulsifying the curcumin-vitamin C-ascorbyl palmitate co-crystal and a wall material colloidal solution under vacuum, sequentially conducting a two-stage wet grinding, a homogenization and a potential adjustment to obtain an emulsified body; and C) subjecting the emulsified body to microencapsulation with a wall material twice and drying to obtain the water-soluble curcumin mixture.

The curcumin-vitamin C-ascorbyl palmitate co-crystal is first prepared. Specifically, curcumin, VC and ascorbyl palmitate are dissolved in an ethanol aqueous solution to obtain a mixed solution. The mass ratio of curcumin, VC and ascorbyl palmitate is 100:(0.001-30):(0.001-30), preferably 100:(0.001-5):(0.001-5). The ethanol aqueous solution has a volume concentration (V/V) of 70% to 99%, preferably 90% to 95%. The temperature of the dissolution is 0-60° C., preferably 25° C.-40° C.

The mixed solution is then evaporated under reduced pressure and ethanol is dried under vacuum to obtain curcumin-VC-ascorbyl palmitate co-crystal. The temperature of the reduced pressure evaporation is: 40° C. to 90° C., and the vacuum pressure is ≤0.02 MPa, and the vacuum pressure is preferably 0.07 MPa to 0.095 MPa.

The pressure of the vacuum drying is from 0.05 MPa to 1.0 MPa, preferably from 0.075 MPa to 0.095 MPa, and the temperature is from 25° C. to 100° C., preferably from 55° C. to 85° C.

In the present invention, VC, ascorbyl palmitate and curcumin can effectively protect curcumin by forming a co-crystal, reducing the oxidative degradation of curcumin, and at the same time can promote better combination of curcumin with wall colloids and fillers to improve the water solubility.

The curcumin-VC-ascorbyl palmitate co-crystal and a wall material colloidal solution are vacuum high-speed emulsified, and sequentially subjected to a two-stage wet grinding, ultra-high pressure homogenization and potential adjustment to obtain an emulsified body.

The wall material colloidal solution is prepared according to the following method:

Deionized water, a wall material colloid material and a filler are mixed to obtain the wall material colloid solution.

The wall material colloid is sodium octenyl succinate, hydroxypropyl starch, acetate starch, carboxymethyl starch, phosphate starch, arabic gum, ghatti gum, xanthan gum, pullulan, fucoidan, trehalose, lactose, or a combination thereof.

The filler is maltodextrin, microcrystalline cellulose, lactitol, erythritol, maltitol, sorbitol, α-cyclodextrin, β-cyclodextrin, γ-cyclodextrin or a combination thereof.

The wall material colloid solution has a wall material colloid concentration of 5 wt % to 65 wt %, preferably 15 wt % to 50 wt %, more preferably 25 wt % to 40 wt %, and has a filler concentration of 5 wt % to 65 wt %, preferably 15 wt % to 50 wt %, more preferably 25 wt % to 40 wt %.

After the wall material colloidal solution is obtained, the curcumin-VC-ascorbyl palmitate co-crystal and the wall material colloidal solution are vacuum high-speed emulsified, followed by a two-stage wet grinding, ultra-high pressure homogenization and potential adjustment to obtain an emulsified body.

The vacuum high-speed emulsification is conducted at a pressure of 0.04 MPa-0.1 MPa, preferably 0.075 MPa-0.095 MPa at 10° C.-90° C., preferably 25° C.-60° C. until the material liquid is evenly dispersed and the fluidity is good.

The two-stage wet grinding includes a first grinding and a second grinding. The diameter of the zirconia beads for the first-stage grinding is: 0.3 mm~0.4 mm, and the grinding speed is 500 rpm~3500 rpm, preferably 1000~3000 rpm, more preferably 1500-2500 rpm, grinding time 1~10 hours, preferably 3~8 hours, primary grinding to emulsion particle size D90≤0.7 um; the diameter of the secondary grinding zirconia beads: 0.1 mm~0.2 mm, grinding speed It is 500 rpm to 3500 rpm, preferably 1000 to 3000 rpm, more preferably 1500 to 2500 rpm, the grinding time is 1 to 10 hours, preferably 3 to 8 hours, and the secondary grinding is performed until the emulsion particle size D90≤0.3 um.

The pressure used for the ultra-high pressure homogenization is 100 MPa-200 MPa, preferably 130 MPa-180 MPa;

The zeta potential modifier for potential adjustment is sodium hexametaphosphate, sodium polyphosphate, sodium pyrophosphate, sodium tripolyphosphate or a combination thereof, and the colloidal emulsion potential is adjusted to −10 mV to −60 mv, preferably −30 mv to −50 mv.

Finally, the emulsified body is subjected to microencapsulation with a wall material twice and drying with a wall material to obtain the water-soluble curcumin mixture.

The wall material is starch, maltodextrin, or a mixture thereof. Preferably, the DE value of the maltodextrin is 5-20.

The drying inlet air temperature is 160° C. to 200° C., the outlet air temperature is 70° C. to 100° C., and the bottom air temperature is 70° C. to 90° C.

In the present invention, the water-soluble curcumin mixture has a curcumin-VC-ascorbyl palmitate co-crystal concentration of 0.01 wt % to 70 wt %, preferably 5 wt % to 40 wt %.

The invention also provides a water-soluble curcumin mixture prepared by the above preparation method.

The invention also provides an application of the above-mentioned water-soluble curcumin mixture in food, health food or medicine. Among them, the present invention has no special restrictions on the form of the food, and it can be added to liquid food or solid food, preferably beverage. In the present invention, there is no special restriction on the dosage form of the health food, and it can be a capsule or a tablet.

The present invention has the following beneficial effects:

1. The present invention discloses a co-crystal of VC, ascorbyl palmitate and curcumin, which can effectively protect curcumin and reduce the oxidative degradation of curcumin. At the same time, the curcumin-VC-ascorbyl palmitate co-crystal can improve the water solubility of curcumin;

2. The present invention adopts a preparation method without synthetic emulsifier and solvent-free in the preparation process. The obtained product does not have the problems of quality safety and application completeness. The preparation process is safer, which is beneficial to the industrialized production of the product;

3. The invention adopts an effective combination of vacuum emulsification technology, two-stage wet grinding, and ultra-high pressure homogenization technology, which can effectively reduce the particle size of curcumin and improve the water solubility of curcumin;

4. The invention adopts phosphate to adjust the Zeta potential at the stage of emulsion preparation completion, which is more conducive to the stability of the curcumin emulsion and ensures the quality uniformity of the curcumin mixture product.

To further understand the present invention, the high-bioavailability water-soluble curcumin mixture provided by the present invention and its preparation method and application are described below in conjunction with examples. The protection scope of the present invention is not limited by the following examples.

Example 1

Weighing 100 g of 93% curcumin, dissolving it in 1000 g of 95% ethanol under stirring, slowly adding 1.0 g of VC and 1.0 g of ascorbyl palmitate, and slowly heating the mixture to 35° C. to 40° C., slowly stirring until completely dissolved. The temperature of the mixture was heated to 65° C. to 75° C., and ethanol was evaporated under a vacuum of 0.08 MPa to obtain a dark yellow viscous substance. The viscous substance was transferred to a vacuum drying oven and dried for 12 hours in an environment of 0.09 MPa and 75° C. to 80° C. The solvent residue was detected to be ≤50 ppm to obtain a VC-ascorbyl palmitate-curcumin co-crystal.

Weighing 50 g of arabic gum, 5 g of ghatti gum, 10 g of α-cyclodextrin, and 110 g of maltodextrin, and dissolving them in 467 g of deionized water to prepare a water-soluble colloidal solution A with a concentration of 30% by weight. Weighing 25 g of VC-ascorbyl palmitate-curcumin co-crystal, adding it to the water-soluble colloidal solution A, keeping the material at 35° C. to 40° C., and emulsifying for 50 minutes under emulsification tank vacuum of 0.085 MPa. The curcumin was uniformly dispersed and the fluidity was good. Curcumin emulsion B was obtained.

Putting the curcumin emulsion B into a wet grinding equipment for a first grinding. The grinding medium was 0.3 mm-0.4 mm zirconia beads. Grinding at 1200 rpm for 4 hours until the particle size D90 was less than 0.7 um. Then carrying out a second grinding. The grinding medium was 0.1 mm-0.2 mm zirconia beads, and the grinding was carried out at 900 rpm for 3 hours until the particle size D90 was less than or equal to 0.3 um, and curcumin emulsion C was obtained.

The curcumin emulsion C was subjected to ultra-high pressure homogenization under a pressure of 156 MPa to obtain a uniform and stable curcumin emulsion D. Preparing 5% sodium hexametaphosphate solution with deionized water, adjusting the Zeta potential of curcumin emulsion D to −38 mv, and obtaining curcumin emulsion E. Using starch as the microcapsule coating material, performing microcapsule drying twice, drying under the conditions of the inlet air temperature at 160° C.-200° C., the outlet air temperature at 70° C.-100° C., and the bottom air temperature at 70° C.-90° C., to obtain the water-soluble curcumin mixture.

The above water-soluble curcumin mixture was dispersed in water. FIG. 1 is a photo showing the solubility of the water-soluble curcumin mixture prepared in Example 1 in water.

The testing showed that the water-soluble curcumin mixture had excellent water solubility. The curcumin content was 10.5%, and the D90 particle size was 278 nm. An aqueous solution with a concentration of 1% by weight was left at room temperature for 4 days without precipitation.

After experimental testing in rats, the bioavailability test method of water-soluble curcumin mixture was verified according to the "Guidelines for Validation of 9012 Biological Sample Quantitative Analysis Method" in the fourth appendix of the Pharmacopoeia of the People's Republic of China (2015 Edition). Specific steps are as follows:

24 Healthy SD (spontaneous mutant Danforth's short tail) rats were randomly divided into 4 groups (6 in each group) after being adaptively reared for one week;

According to the dose of 200 mg·kg$^{-1}$ (calculated as curcumin) for intragastric administration, the first group and the third group were given curcumin (raw material), and the second and fourth groups were given the water-soluble curcumin mixtures of Example 1 and Example 2, respectively;

In each group, about 0.3 mL of blood was collected from the orbit at 0.167, 0.5, 1, 1.5, 2, 3, 5, 8 and 12 hours after administration, and centrifuged at 4000 rpm for 10 minutes. The plasma was stored at −20° C. for later use.

Separating 100 μL of plasma, adding 0.3 mL of ethyl acetate, mixing for 2 min, centrifuging at 4000 rpm for 10 min, and separating the supernatant; adding 0.3 mL of ethyl acetate to the precipitate, mixing for 2 min, and centrifuging at 4000 rpm for 10 min, vacuum drying at 40° C. Adding 100 μL of methanol to the residue, wetting the centrifuge tube, mixing for 2 min, filtering with 0.22 μm microporous membrane, analyzing and testing.

HPLC-MS/MS with emodin as the internal standard was used for detection, and DAS2.0 software was used to calculate the pharmacokinetic parameters and compare the relative bioavailability. The results are as follows:

TABLE 1

Bioavailability Test Results

| | First Group: curcumin | Second Group: Mixture of Example 1 | Third Group: curcumin | Second Group: Mixture of Example 2 |
|---|---|---|---|---|
| AUC (012 h) (ng/ml * h) | 108.1 | 1111.5 | 140.36 | 2591.35 |

TABLE 1-continued

Bioavailability Test Results

| | First Group: curcumin | Second Group: Mixture of Example 1 | Third Group: curcumin | Second Group: Mixture of Example 2 |
|---|---|---|---|---|
| Relative Bioavailability (%) | / | 1028.21 | / | 1846.22 |

Figure 3:
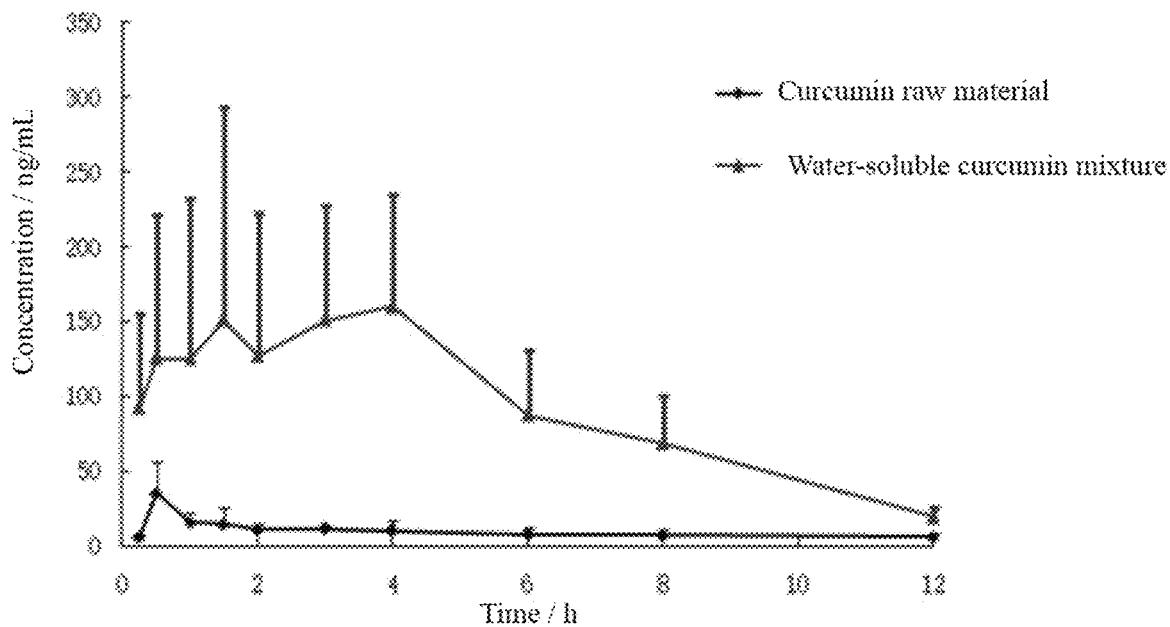
FIG. 3 shows the relative bioavailability test results of the curcumin mixture of Example 1.

The bioavailability of the water-soluble curcumin mixture relative to curcumin raw materials increased by 10.28 times (the relative bioavailability "blood concentration curve" is shown in FIG. 3).

Example 2

Weighing 200 g of 93% curcumin and dissolving it in 3000 g of 95% ethanol under stirring, slowly adding 3.0 g of VC and 3.5 g of ascorbyl palmitate, slowly heating the mixture to 35° C. to 40° C., slowly stirring until completely dissolved. The mixture was heated to 65° C. to 75° C., and the ethanol was evaporated under a vacuum of 0.08 MPa to obtain a dark yellow viscous substance. The viscous substance was transferred to a vacuum drying oven and dried for 15 hours under 0.09 MPa and 75° C. to 80° C. The solvent residue was detected to be less than 50 ppm to obtain a VC-ascorbyl palmitate-curcumin co-crystal.

Weighing 70 g sodium octenyl succinate starch, 5 g arabic gum, 20 g γ-cyclodextrin, 45 g maltodextrin, and 20 maltitol, dissolving them in 467 g deionized water to form a water-soluble colloidal solution A with a concentration of 26 wt %. Weighing 38 g of VC-ascorbyl palmitate-curcumin co-crystal, add it to the water-soluble colloidal solution A, keeping the mixture at 35° C. to 40° C., and emulsifying for 45 minutes under the conditions of 0.085 MPa in the emulsifying tank. The curcumin was uniformly dispersed and the fluidity is good, and curcumin emulsion B was obtained.

Adding the curcumin emulsion B into a wet grinding equipment for a first grinding. The grinding medium was 0.3 mm-0.4 mm oxidized pickaxe beads. Grinding at a speed of 1100 rpm for 6 hours until the particle size D90 was less than 0.7 um. Then carrying out a second grinding. The grinding medium was 0.1 mm to 0.2 mm oxidized pickaxe beads, grinding at 1000 rpm rotation speed for 3 hours, until the particle size D90 was less than 0.3 um, and curcumin emulsion C was obtained. Under 180 MPa pressure, the curcumin emulsion C was subjected to ultra-high pressure homogenization to obtain a uniform and stable curcumin emulsion D. Preparing 5% sodium hexametaphosphate solution with deionized water, adjusting the Zeta potential of curcumin emulsion D to −30 mv, and obtaining curcumin emulsion E. Using starch as the microcapsule coating material, performing microcapsule drying twice, drying under the conditions of the inlet air temperature at 160° C.-200° C., the outlet air temperature at 70° C.-100° C., and the bottom air temperature at 70° C.-90° C., to obtain the water-soluble curcumin mixture.

Test results showed that the water-soluble curcumin mixture had excellent water solubility, the curcumin content was 21.3%, the D90 particle size was 260 nm, and the aqueous solution with a concentration of 1 wt % was placed at room temperature for 4 days without precipitation.

Figure 4:
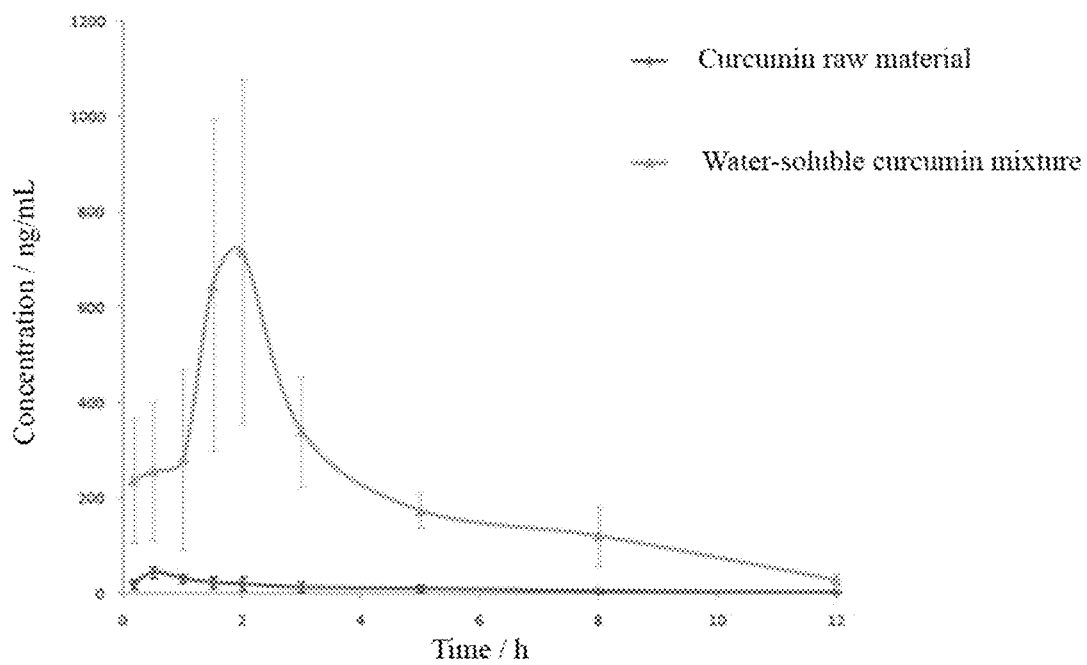
FIG. 4 shows the relative bioavailability test results of the curcumin mixture of Example 2.

After experimental tests in rats (implemented in accordance with the "Technical Guidelines for Preclinical Pharmacokinetic Research"), the bioavailability of the water-soluble curcumin mixture relative to curcumin raw materials increased by 18.46 times (relative bioavailability "blood drug concentration curve" see FIG. 4).

Example 3

Weighing 250 g of curcumin with 93% content and dissolving it in 3500 g of 95% ethanol under stirring, slowly adding 2.5 g of VC and 3.5 g of ascorbyl palmitate, slowly heating the mixture to 35° C.-40° C., slowly stirring until completely dissolved. The mixture was heated to 65° C. to 75° C., and the ethanol was evaporated under a vacuum of 0.08 MPa to obtain a dark yellow viscous substance. The viscous substance was transferred to a vacuum drying oven and dried for 16 hours in an environment of 0.09 MPa and 75° C. to 80° C., and the solvent residue was detected to be less than 50 ppm to obtain a VC-ascorbyl palmitate-curcumin co-crystal.

Weighing 50 g of sodium octenyl succinate starch, 1.5 g of hydroxypropyl starch, 10 g of pullulan, 30 g of trehalose, 52.5 g of maltodextrin and dissolving them in 512 g of deionized water to form a water-soluble colloidal solution A with a concentration of 25 wt %. Weighing 62 g of VC-ascorbyl palmitate-curcumin co-crystal and adding it to the water-soluble colloidal solution A. Keeping the mixture at 35° C. to 40° C. and emulsifying it for 60 minutes under the conditions of 0.085 MPa in the emulsifying tank. The curcumin was uniformly dispersed and the fluidity was good, and curcumin emulsion B was obtained.

Adding the curcumin emulsion B into a wet grinding equipment for a first grinding. The grinding medium was 0.3 mm-0.4 mm zirconia beads. Grinding at a speed of 1000 rpm for 4 hours until the particle size D90 was less than 0.7 um. Then carrying out a second grinding, the grinding medium was 0.1 mm-0.2 mm zirconia beads, grinding at 1100 rpm rotation speed for 3 hours, until the particle size D90 was less than 0.3 um. The curcumin emulsion C was obtained.

Under the pressure of 175 Mpa, the curcumin emulsion C was subjected to ultra-high pressure homogenization to obtain a uniform and stable curcumin emulsion D. Preparing 5% sodium hexametaphosphate solution with deionized water, adjusting the Zeta potential of curcumin emulsion D to −35 mv, and obtaining curcumin emulsion E. Using starch as the microcapsule coating material, performing microcapsule drying twice, drying under the conditions of the inlet air temperature at 160° C.-200° C., the outlet air temperature at 70° C.-100° C., and the bottom air temperature at 70° C.-90° C., to obtain the water-soluble curcumin mixture. Testing results showed that the water-soluble curcumin mixture had excellent water solubility, the curcumin content was 30.5%, and the D90 particle size was 286 nm. An aqueous solution with a concentration of 1% by weight was left at room temperature for 4 days without precipitation.

Comparative Example 1

Curcumin Raw Materials

Figure 2:
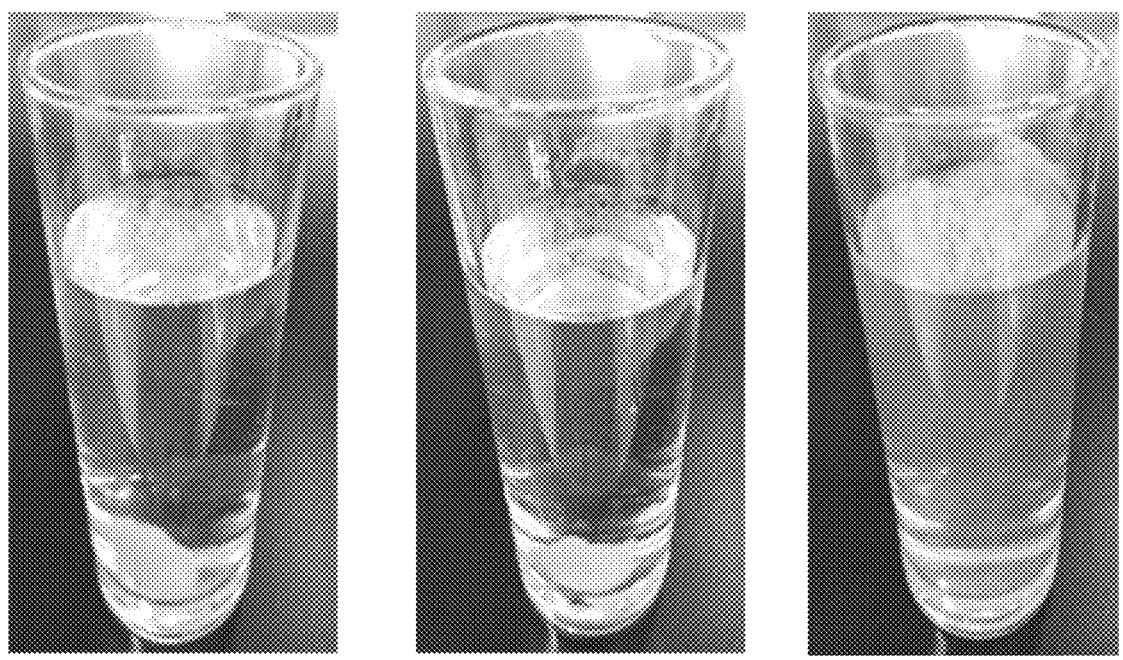
FIG. 2 is a photo showing the solubility of the curcumin raw material of Comparative Example 1 in water.

The curcumin raw material was dispersed in water, and the result is shown in FIG. 2. FIG. 2 is a photo of solubility of the curcumin raw material in water. It can be seen from FIG. 2 that curcumin is insoluble in water.

Comparative Example 2

According to the process of Example 3, 93% curcumin was directly used as the raw material for the preparation test. The process and results are as follows:

Weighing 50 g of sodium octenyl succinate starch, 1.5 g of hydroxypropyl starch, 10 g of pullulan, 30 g of trehalose, 52.5 g of maltodextrin and dissolving them in 512 g of deionized water to obtain a water-soluble colloidal solution A with a concentration of 25 wt %. Weighing 60.55 g of 93% curcumin and adding it to the water-soluble colloidal solution A. Keeping the mixture at 35° C. to 40° C. and emulsifying the mixture at 0.085 MPa for 60 minutes until the curcumin was evenly dispersed and the fluidity was good. Curcumin emulsion B was obtained.

Adding the curcumin emulsion B into a wet grinding equipment for a first grinding. The grinding medium was 0.3 mm-0.4 mm zirconia beads. Grinding at a speed of 1000 rpm for 4 hours until the particle size D90 was less than 0.7 um. Then carrying out a second grinding, the grinding medium was 0.1 mm-0.2 mm zirconia beads, grinding at 1100 rpm rotation speed for 3 hours, until the particle size D90 was less than 0.3 um, the curcumin emulsion C was obtained.

Under the pressure of 175 MPa, the curcumin emulsion C was subjected to ultra-high pressure homogenization to obtain a uniform and stable curcumin emulsion D. Preparing 5% sodium hexametaphosphate solution with deionized water, adjusting the Zeta potential of curcumin emulsion D to −35 mv, and obtaining curcumin emulsion E. Using starch as the microcapsule coating material, performing microcapsule drying twice, drying under the conditions of the inlet air temperature at 160° C.-200° C., the outlet air temperature at 70° C.-100° C., and the bottom air temperature at 70° C.-90° C., to obtain a curcumin mixture.

After testing, the curcumin content was 28.1%, the D90 particle size was 628 nm, and the curcumin mixture was generally water-soluble. For the 1 wt % aqueous solution, curcumin precipitate appeared after being left for 2 hours.

Comparative Example 3

According to the process of Example 1, except that the curcumin emulsion D did not adjust the Zeta potential, and the test was carried out. The process and results are as follows:

Weighing 100 g of curcumin with 93% content and dissolving it in 1000 g of 95% ethanol under stirring. Slowly adding 1.0 g of VC and 1.0 g of ascorbyl palmitate. During the process, slowly heating the mixture to 35° C. to 40° C., stirring slowly until completely dissolved. The mixture was heated to 65° C. to 75° C., and the ethanol was evaporated under a vacuum of 0.08 MPa to obtain a dark yellow viscous substance. The viscous material was transferred to a vacuum drying oven, and dried for 12 hours at 0.09 MPa and 75° C. to 80° C., and the solvent residue was determined to be less than 50 ppm to obtain VC-ascorbic thrombopalmitate-curcumin co-crystal.

Weighing 50 g of arabic gum, 5 g of ghatti gum, 10 g of α-cyclodextrin, and 110 g of maltodextrin, and dissolving them in 467 g of deionized water to prepare a water-soluble colloidal solution A with a concentration of 30 wt %. Weighing 25 g of VC-ascorbic thrombus palmitate-curcumin co-crystal, adding it to the water-soluble colloidal solution A, keeping the mixture at 35° C.-40° C., and emulsifying for 50 minutes under the conditions of emulsification tank vacuum of 0.085 MPa, until the curcumin was uniformly dispersed and the fluidity was good, and curcumin emulsion B was obtained.

Adding the curcumin emulsion B into a wet grinding equipment for a first grinding. The grinding medium was 0.3 mm to 0.4 mm zirconia beads. Grinding at 1200 rpm for 4 hours until the particle size D90 was less than 0.7 um. Then carrying out a second grinding, the grinding medium was 0.1 mm-0.2 mm zirconia beads, and the grinding was carried out at 900 rpm for 3 hours until the particle size D90 was less than or equal to 0.3 um, and curcumin emulsion C was obtained. The curcumin emulsion C was subjected to ultra-high pressure homogenization under a pressure of 156 Mpa to obtain a uniform and stable curcumin emulsion D.

After placing the curcumin emulsion D for 10-12 hours, the emulsion showed signs of layering. After stirring, starch was used as the microcapsule coating material, performing microcapsule drying twice, drying under the conditions of the inlet air temperature at 160° C.-200° C., the outlet air temperature at 70° C.-100° C., and the bottom air temperature at 70° C.-90° C., to obtain a curcumin mixture.

After testing, the curcumin content was 10.12%, the D90 particle size was 432 nm, and the water solubility was good. A little curcumin precipitated after being placed for 10 to 12 hours in an aqueous solution with a concentration of 1 wt %.

Comparative Example 4

According to the process plan of Example 1, except that the curcumin emulsion C was homogenized under a pressure of 80 MPa, and the test was carried out. The process and results are as follows:

Weighing 100 g of curcumin with 93% content and dissolving it in 1000 g of 95% ethanol under stirring. Slowly adding 1.0 g of VC and 1.0 g of ascorbyl palmitate. During the process, slowly heating the mixture to 35° C.-40° C., stirring slowly until completely dissolved. The mixture was heated to 65° C. to 75° C., and the ethanol was evaporated under a vacuum of −0.08 Mpa to obtain a dark yellow viscous substance. The viscous material was transferred to a vacuum drying oven, and dried for 12 hours at 0.09 MPa and 75° C. to 80° C., and the solvent residue was determined to be less than 50 ppm to obtain VC-ascorbic thrombopalmitate-curcumin co-crystal.

Weighing 50 g of arabic gum, 5 g of ghatti gum, 10 g of α-cyclodextrin, and 110 g of maltodextrin, and dissolving them in 467 g of deionized water to prepare a water-soluble colloidal solution A with a concentration of 30 wt %. Weighing 25 g of VC-ascorbic thrombus palmitate-curcumin co-crystal, adding it to the water-soluble colloidal solution A, keeping the mixture at 35° C. to 40° C., and emulsifying for 50 minutes under the conditions of emulsification tank vacuum of 0.085 MPa, until the curcumin was uniformly dispersed and the fluidity was good, and curcumin emulsion B was obtained.

Adding the curcumin emulsion B into the wet grinding equipment for a first grinding. The grinding medium was 0.3 mm to 0.4 mm zirconia beads. Grinding at 1200 rpm for 4 hours until the particle size D90 is less than 0.7 um. Then carrying out a second grinding, the grinding medium was 0.1 mm to 0.2 mm zirconia beads, and the grinding was carried out at 900 rpm for 3 hours until the particle size D90 was less than or equal to 0.3 um, and curcumin emulsion C weas obtained.

The curcumin emulsion C was subjected to ultra-high pressure homogenization under a pressure of 80 Mpa to obtain a uniform and stable curcumin emulsion D. Preparing 5% sodium hexametaphosphate solution with deionized water, adjusting the Zeta potential of curcumin emulsion D to −38 mv, and obtaining curcumin emulsion E. Using starch as the microcapsule coating material, performing microcapsule drying twice, drying under the conditions of the inlet air temperature at 160° C.-200° C., the outlet air temperature at 70° C.-100° C., and the bottom air temperature at 70° C.-90° C., to obtain a curcumin mixture.

After testing, the curcumin mixture has good water solubility, the curcumin content was 10.3%, the D90 particle size weas 398 nm, and the aqueous solution with a concentration of 1 wt % had a little curcumin precipitation after being placed for 10 to 12 hours.

The above are only the preferred embodiments of the present invention. It should be pointed out that for those of ordinary skill in the art, without departing from the principle of the present invention, several improvements and modifications can be made, and these improvements and modifications are also It should be regarded as the protection scope of the present invention.

The invention claimed is:

1. A method for preparing a water-soluble curcumin mixture with high bioavailability, comprising the following steps:
    A) dissolving curcumin, vitamin C and ascorbyl palmitate in a water-ethanol mixture, evaporating ethanol under reduced pressure, and vacuum drying to obtain a curcumin-vitamin C-ascorbyl palmitate co-crystal;
    B) high-speed emulsifying the curcumin-vitamin C-ascorbyl palmitate co-crystal and a wall material colloidal solution under vacuum, sequentially conducting a two-stage wet grinding, a homogenization and a potential adjustment to obtain an emulsified body; and
    C) subjecting the emulsified body to microencapsulation with a wall material and drying twice to obtain the water-soluble curcumin mixture.

2. The method according to claim 1, wherein a mass ratio of curcumin, vitamin C and ascorbyl palmitate is 100:(0.001-30):(0.001-30).

3. The method according to claim 1, wherein in step A), curcumin, vitamin C, ascorbyl palmitate and the water-ethanol mixture are heated at 35° C. to 40° C.; ethanol is evaporated under a pressure of from 0.05 MPa to 1.0 MPa and at 25° C. to 100° C.

4. The method according to claim 1, wherein the wall material colloid solution comprises one or more compounds selected from the group consisting of sodium starch octenyl succinate, hydroxypropyl starch, acetate starch, carboxymethyl starch, phosphate starch, arabic gum, ghatti gum, xanthan gum, pullulan, fucoidan, trehalose, and lactose; the wall material colloidal solution further comprises a filler, and the filler is selected from the group consisting of maltodextrin, microcrystalline cellulose, lactitol, erythritol, maltitol, sorbitol, α-cyclodextrin, β-cyclodextrin, γ-cyclodextrin, and a combination therefore; and
    the wall material colloid solution has a wall material colloid concentration of from 5 wt % to 65 wt % and the filler concentration of from 5 wt % to 65 wt %.

5. The method according to claim 1, wherein the two-stage wet grinding comprises a first grinding and a second grinding; the first grinding uses zirconia beads with diameter of 0.3 mm-0.4 mm and is conducted at a speed of from 500 rpm to 3500 rpm for 1 to 10 hours; and the second grinding uses zirconia beads with diameter of 0.1 mm-0.2 mm and is conducted at a speed of 500 rpm to 3500 rpm for from 1 hour to 10 hours.

6. The method according to claim 1, wherein the high-speed emulsifying is conducted under a pressure of 0.05 MPa-0.1 Mpa, and at 10° C.-90° C.;
    the homogenization is conducted under 100 MPa-200 MPa; and
    the potential adjustment uses a Zeta potential modifier selected from the group consisting of sodium hexametaphosphate, sodium polyphosphate, sodium pyrophosphate, and sodium tripolyphosphate, and a colloidal emulsion potential is adjusted to from −10 mv to −60 mv.

7. The method according to claim 1, wherein the wall material is starch, maltodextrin, or a mixture thereof, and a dextrose equivalent value of maltodextrin is 5-20; and wherein the microencapsulation is conducted at a drying inlet air temperature of from 160° C. to 200° C., an outlet air temperature of from 70° C. to 100° C., and a bottom air temperature of from 70° C. to 90° C.

8. The method according to claim 1, wherein the water-soluble curcumin mixture has a curcumin-vitamin C-ascorbyl palmitate co-crystal concentration of from 5 wt % to 40 wt %.

9. A water-soluble curcumin mixture prepared by the method according to claim 1.

* * * * *